United States Patent [19]
Kim et al.

[11] Patent Number: 5,874,572
[45] Date of Patent: Feb. 23, 1999

[54] PROCESS FOR PREPARING CYCLOSPORIN A

[75] Inventors: Jung Woo Kim; Nam Hee Choi, both of Seoul; Sang Chul Lee, Kyeonggi-Do; Gang Sun Choi, Kyeonggi-Do; Yun Beom Ham, Kyeonggi-Do; Don Wha Lee, Kyeonggi-Do; Kyeong Bok Min, Seoul, all of Rep. of Korea

[73] Assignee: Chong Kun Dang Corp., Seoul, Rep. of Korea

[21] Appl. No.: 817,205

[22] PCT Filed: Jul. 31, 1995

[86] PCT No.: PCT/KR95/00095

§ 371 Date: Jun. 16, 1997

§ 102(e) Date: Jun. 16, 1997

[87] PCT Pub. No.: WO96/12031

PCT Pub. Date: Apr. 25, 1996

[30] Foreign Application Priority Data

Oct. 13, 1994 [KR] Rep. of Korea .................. 1994-26200

[51] Int. Cl.⁶ .......................... C12P 21/04; C07D 259/00; C07D 257/00
[52] U.S. Cl. .......................... 540/460; 540/450; 540/451; 435/71.1; 435/71.3; 530/317; 530/321
[58] Field of Search .................................. 435/71.1, 71.3; 530/317, 321; 540/450, 451, 460

[56] References Cited

U.S. PATENT DOCUMENTS

| 4,117,118 | 9/1978 | Härri et al. ............................... 424/177 |
| 4,215,199 | 7/1980 | Härri et al. ................................. 435/71 |
| 5,156,960 | 10/1992 | Jekkel née Bokány et al. ...... 435/71.1 |
| 5,256,547 | 10/1993 | Rudat et al. ............................ 435/71.1 |

FOREIGN PATENT DOCUMENTS

| 298 276 | 2/1992 | Germany . |
| 1 491 509 | 11/1977 | United Kingdom . |

*Primary Examiner*—Mukund J. Shah
*Assistant Examiner*—Pavanaram K Sripada
*Attorney, Agent, or Firm*—Finnegan, Henderson, Farabow, Garrett & Dunner, L.L.P.

[57] ABSTRACT

A process for the isolation of cyclosporin A comprising the steps of: adding a lower alkanol solvent to a culture fluid of a mutant of *Tolypocladium inflatum* to form a mixture, filtering the mixture to form an extract, transferring the extract to methylene chloride as a solvent therefor, and column chromatographing the resultant product on silica gel.

3 Claims, No Drawings

PROCESS FOR PREPARING CYCLOSPORIN A

TECHNICAL FIELD

The present invention relates to a novel process for the preparation of cyclosporin A represented by following structural formula(I).

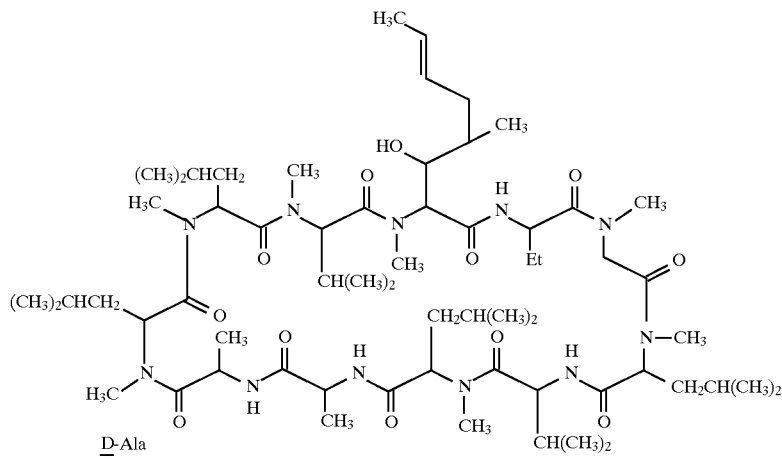

Cyclosporin A represented by the above structural formula is a cyclic peptide of molecular weight 1202, molecular formula $C_{62}H_{111}N_{11}O_{12}$, consisting of eleven(11) amino acids, and obtained from a culture fluid of *Tolypocladium inflatum*, a strain producing cyclosporin A. There are twenty five(25) derivatives of cyclosporin A dependent upon the types of amino acids [Traber R., HELVETICA ACTA, 70, 13(1987)].

Chemical name of cyclosporin A is cyclo[{(E)-(2S,3R,4R)-3-hydroxy-4-methyl-2-(methylamino)-octenoyl}-L-2-aminobutyryl-N-methyl-glycyl-N-methyl-L-leucyl-L-valyl-N-methyl-L-leucyl-L-alanyl-O-alanyl-N-methyl-L-leucyl-N-methyl-L-leucyl-N-methyl-L-valyl]. Showing very strong immunosuppressive effect, cyclosporin A has been used for suppressing rejection symptoms and treating auto-immune diseases. Also, it is known to have antifungal, insecticidal and anti-inflammatory effect [Borel J. F., Prog. Allergy, 38, 9(1986)].

BACKGROUND ART

As prior arts concerning the process for preparing cyclosporin A, methods using fermentation by *Cylindrocarpon lucidum* and *Tolypocladium inflatum* are disclosed in GB Patent 1,491,509 and U.S. Pat. No. 4,117,118, and U.S. Pat. No. 4,215,199. Also, various methods to recover cyclosporin A from the culture fluid are disclosed in these patents.

In the above-mentioned patents, a process comprising the steps of extracting mycellium isolated from the culture fluid with a solvent, and then recovering the product by successively using chromatography media such as sephadex, aluminum oxide and silica gel has been used as a process for recovering cyclosporin A from the culture fluid. In accordance with these processes, solvent is added to mycellium as isolated solid obtained by filtering the culture fluid; the mixture is extracted by solvent by means of centrifugal extracter; the resultant extract is pretreated with water or hexane or the like; and then the product is purified through chromatography media such as sephadex, aluminum oxide and silica gel, etc. to obtain cyclosporin A. However, the procedure is complicated because two or three types of chromatography media including sephadex should be used after extracting the mycellium as isolated solid obtained by filtering the culture fluid with solvent. Besides, the processes may cause problems of process economics and environmental pollution because each eluting solvent shoud be used for each chromatography procedure.

Thus, in order to overcome the complexity of the processes and lighten the economic burden, various methods for purifying cyclosporin A have been studied.

For example, according to the teachings of U.S. Pat. No. 5,256,547 and European Patent 507,968 A1, mycellium as isolated solid obtained by filtering the culture fluid is dried and then extracted with a solvent to obtain crude cyclosporin A; the product is pretreated without washing with water or the like, and purified by means of chromatography using aluminum oxide and silica gel avoiding the use of expensive sephadex to obtain cyclosporin A. In addition, according to the teachings of U.S. Pat. No. 5,156,960, the culture fluid is extracted by directly adding solvent, the extract is transferred to a solvent having higher solubility and dried over a drying agent such as anhydrous magnesium sulfate, and the resultant product is purified by chromatography through sephadex and silica gel etc. to obtain cyclosporin A.

Although the art described in U.S. Pat. No. 5,256,547 has advantages in that content of pigment has been reduced by virtue of the solvent extraction and the process has been simplified in the course of solvent pretreatment and chromatography, it also has disadvantage in that an extra process for drying the mycellium should be performed. On the other hand, the art described in U.S. Pat. No. 5,156,960 has an advantage in that solvent extraction is carried out directly from the culture fluid by simply adding a solvent instead of solvent extraction from mycellium separated from the culture fluid after filtration, and the processes through chromatography media are performed without pretreatment with solvent. However, there should be an additional process for drying over expensive anhydrous magnesium sulfate because a significant amount of moisture is admixed in the transferring solvent owing to the curtailment of the process, and two chromatography media of sephadex and silica gel are used so that it still involves problems of complexity and economic disadvantage so as to be industrialized.

DISCLOSURE OF INVENTION

The present inventors have intensively studied to solve the problems of the prior art, and completed a novel economic process for preparing cyclosporin A comprising the steps of solvent extraction by directly adding a solvent to the culture fluid instead of the solvent extraction of mycellium isolated by filtering the culture fluid; and single chromatography using silica gel media without drying process using anhydrous magnesium sulfate.

The present invention relates to a process for the preparation of cyclosporin A comprising the steps of adding alkanol solvent to a culture fluid of a mutant of *Tolypocladium inflatum* and extracting the mixture; transferring the extract to methylene chloride having higher solubility; treating the solution with activated charcoal; and the resultant product being column chromatographed on silica gel.

During the extraction process of the culture fluid, alkanol solvent is used. The amount of the alkanol solvent to be added is desirably about twice by volume of the culture fluid, and extraction is preferably carried out for about 30 minutes with stirring.

Among these solvents, methylene chloride is preferably used. Prior to the treatment through chromatography media, it is preferred to treat the product with activated charcoal in order to remove the colored impurity.

In the process according to the present invention, drying process which have been the big problem of the prior art to be industrialized is omitted, and the moisture content of the extracted solution is far lowered by using methylene chloride.

In addition, the purity of the cyclosporin A was improved by virtue of the choice of methylene chloride as a transferring solvent and the treatment with activated charcoal, and a significant amount of solvent is saved because of the simplification of the chromatography procedure so that lessen the environmental burden.

BEST MODE FOR CARRYING OUT THE INVENTION

Now, the present invention is further described by referring to the following examples. However, the present invention should not be understood to be limited to the examples.

EXAMPLE 1

Three(3) liters of methanol were added to 1.5 liters of culture fluid containing cyclosporin A(7,115 μg/ml), and the mixture was filtered to collect the extracted cyclosporin A. The extract obtained was washed with 2 liters of hexane, and the product was further extracted by adding 2 liters of methylene chloride. Thirty grams of activated charcoal were added to the mixture in order to remove colored impurity. After filtration, the mixture was evaporated to dryness.

The product obtained was dissolved in 50 ml of ethyl acetate and the solution was loaded to the top of the silica gel column. After eluting the product by ethyl acetate, the combined fractions (3,000 ml) containing the desired product were evaporated to dryness. Three mililiters of ethyl ether were added to dissolve the product, and added 150 ml of methoxymethane to the mixture. The product precipitated was isolated to obtain cyclosporin A (6.4 g, content:98.5–100.0%).

EXAMPLE 2

Three(3) liters of methanol were added to 1.5 liters of culture fluid containing cyclosporin A (6,757 μg/ml), and the mixture was filtered to collect the extracted cyclosporin A. After concentrating the extract to have a volume of 1.1 liter, the concentrate was washed with 1.1 liter of methoxymethane, and the resultant product was extracted twice with 1.1 liter of methylene chloride each.

The product was treated with activated charcoal and chromatographed on silica gel in accordance with Example 1 to obtain cyclosporin A(7.09 g, content:98.5–100.0%).

EXAMPLE 3

The same procedure as Example 1 was repeated but washing the methanol extract with 2 liters of methoxymethane, to obtain cyclosporin A (content:98.5–100.0%).

What is claimed is:

1. A process for the isolation of cyclosporin A comprising the steps of:
   a) adding a lower alkanol solvent to a culture fluid of a mutant of *Tolypocladium inflatum* to form a mixture;
   b) filtering the mixture to form an extract;
   c) transferring the extract to methylene chloride to form a resultant product; and
   d) column chromatographing the resultant product on silica gel to obtain the cyclosporin A.

2. The process of claim 1, wherein the resultant product is treated with activated charcoal prior to being column chromatographed.

3. The process of claim 1, wherein the lower alkanol solvent of step a) is methanol.

* * * * *